United States Patent
Russell

(10) Patent No.: US 10,568,905 B2
(45) Date of Patent: Feb. 25, 2020

(54) PHARMACEUTICAL COMPOSITION AND METHOD FOR TREATING RETINAL NEURODEGENERATION

(71) Applicant: METABOLIC THERAPY INC., Austin, TX (US)

(72) Inventor: Kenneth O. Russell, Austin, TX (US)

(73) Assignee: Metabolic Therapy Inc., Austin, TX (US)

( * ) Notice: Subject to any disclaimer, the term of this patent is extended or adjusted under 35 U.S.C. 154(b) by 0 days.

(21) Appl. No.: 16/511,752

(22) Filed: Jul. 15, 2019

(65) Prior Publication Data

US 2019/0336525 A1 Nov. 7, 2019

Related U.S. Application Data

(63) Continuation-in-part of application No. 13/385,340, filed on Feb. 14, 2012, now Pat. No. 10,398,729, and a continuation-in-part of application No. 16/442,512, filed on Jun. 16, 2019.

(51) Int. Cl.
| | |
|---|---|
| *A61K 33/24* | (2019.01) |
| *A61K 33/06* | (2006.01) |
| *A61K 47/38* | (2006.01) |
| *A61K 9/06* | (2006.01) |
| *A61P 27/02* | (2006.01) |

(52) U.S. Cl.
CPC ............... *A61K 33/24* (2013.01); *A61K 9/06* (2013.01); *A61K 33/06* (2013.01); *A61K 47/38* (2013.01); *A61P 27/02* (2018.01)

(58) Field of Classification Search
CPC .......... A61K 33/24; A61K 9/06; A61K 33/06; A61K 47/38; A61P 27/02
See application file for complete search history.

(56) References Cited

U.S. PATENT DOCUMENTS

| | | | |
|---|---|---|---|
| 9,642,877 B1 * | 5/2017 | Russell | A61K 33/24 |
| 2003/0124176 A1 * | 7/2003 | Hsu | A61K 8/0208 424/449 |
| 2005/0192260 A1 * | 9/2005 | Gyurik | A61K 9/0014 514/171 |
| 2006/0004096 A1 | 1/2006 | Larner | |
| 2008/0181972 A1 | 7/2008 | Amico et al. | |
| 2008/0219913 A1 | 9/2008 | Gogotsi | |
| 2008/0261937 A1 * | 10/2008 | Dudley | A61K 31/568 514/178 |
| 2017/0231925 A1 | 8/2017 | Alkharfy et al. | |

OTHER PUBLICATIONS

Ge Deng, et al., Chromium: Binding Studies With Transferrin and Peptide EEEEGDD and Its Effect on Colorectal Cancer.

* cited by examiner

*Primary Examiner* — Doan T Phan
(74) *Attorney, Agent, or Firm* — Frank Pham; Pham IP Group

(57) ABSTRACT

A pharmaceutical composition useful for preventing and treating retinal neurodegeneration related diseases comprising chromium chloride and magnesium sulfate, thickening agent, penetration enhancer, and pharmaceutical acceptable carrier, diluent or excipient. Further disclosed is a method for treating and preventing retinal neurodegeneration related diseases utilizing the composition.

18 Claims, No Drawings

PHARMACEUTICAL COMPOSITION AND METHOD FOR TREATING RETINAL NEURODEGENERATION

CROSS-REFERENCE TO RELATED APPLICATION

Continuation in-part of application Ser. No. 13/385,340 filed on Feb. 14, 2012, which is a continuation in-part of application Ser. No. 12/069,505, filed on Feb. 11, 2008, now U.S. Pat. No. 9,585,898, and continuation in-part of application Ser. No. 16/442,512 filed on Jun. 16, 2019, the disclosure of which is hereby incorporated by reference herein in its entirety.

FIELD OF INVENTION

The present invention relates to pharmaceutical compositions and methods for treating or preventing retinal neurodegeneration related diseases using the composition to optimize, balance, and regulate transferrin bound iron cell.

BACKGROUND

Iron is essential for cell growth, proliferation and differentiation. Heme-iron is a cofactor for hemoglobin and myoglobin involved in many important physiological processes including oxygen binding and transport, and oxygen metabolism. Non-heme iron is the active center of many important enzymes involved in DNA synthesis and cell cycle (Pantopoulos, K. et al, Regulation of cellular iron metabolism. Biochem. J. 2011, 434, 365-381). Iron is also a necessary cofactor for the synthesis of neurotransmitters, dopamine, norepinephrine, and serotonin, and disruption of iron homeostasis may be involved in Parkinson's disease and/or mood disorders (Youdim, 1990).

Iron deficiency is the most common cause of anemia and represents a global health problem. Iron-deficiency anemia is defined by low numbers of small (microcytic) and hypoferremic erythrocytes. Iron deficiency may contribute to cognitive developmental defects in children, poor physical performance, and unfavorable pregnancy outcomes (Camaschella, 2015). Iron deficiency in children results in auditory defects from disruption of myelin (Roncagliolo et al., 1998), and demylinating diseases such as multiple sclerosis are associated with defects in cellular iron homeostasis (Drayer et al., 1987).

Iron overload is also common and equally detrimental, affecting parenchymal organs including the liver, heart, and pancreas. In Western populations iron overload is mostly genetic due to hereditary hemochromatosis (HH), caused by mutations in genes involved in the sensing of systemic iron levels (such as HFE, HJV, and TFR2), or to disorders that cause ineffective erythropoiesis and secondary iron loading (e.g., thalassemias). There is increasing awareness that acquired metabolic disorders can also cause iron overload, which may exacerbate pathogenesis (Pietrangelo, 2016).

In the retina, iron is particularly important for the visual phototransduction cascade. Photoreceptor cells are constantly shedding and synthesizing their outer segments containing disc membranes. Thus, photoreceptors depend highly on iron-containing enzymes including fatty acid desaturase for synthesis of lipids used in generating new disc membranes (Schichi, 1969).

While iron is necessary for retinal function, excess iron can be harmful. Free $Fe^{2+}$ participates in the Fenton reaction by catalyzing the conversion of hydrogen peroxide to the hydroxyl radical, the most reactive of reactive oxygen species. Hydroxyl radicals are extremely reactive, causing lipid peroxidation, DNA strand breaks, and degradation of biomolecules (Halliwell and Gutteridge, 1984), and have been implicated in the pathogenesis of Alzheimer's and other CNS diseases (Smith et al., 1997).

The retina is isolated from the bloodstream by blood-retinal barriers. The retinal pigment epithelium (RPE) and the neuroretinal vasculature form independent barriers, the intercellular tight junctions of which prevent intercellular diffusion, thereby protecting both sides of the retina from the systemic circulation.

Ferric iron is carried in the bloodstream in association with a protein, transferrin (Baker and Morgan, 1994). Transferrin, with iron, is endocytosed into cells following binding to the cell surface transferrin receptor. The transferrin is found in the retina (Yefimova et al., 2000). Transferrin mRNA expression was detected by in situ hybridization in the RPE cell layer, indicating that the RPE is the main site of transferrin synthesis. Transferrin may carry iron from the RPE to the photoreceptors via a Tf-TfR-dependent mechanism (Yefimova et al., 2000).

Iron bound to transferrin in the choroidal circulation has been shown to be taken up by high-affinity transferrin receptors at the basolateral surfaces of RPE cells. From there, iron is transported to the apical surfaces of RPE cells where it is released to the neural retina.

Increased intraocular iron has been found to cause oxidative damage to the retina. A higher concentration of iron causes the outer border of the outer nuclear layer to become irregular, suggesting photoreceptor damage. People with a deficiency in ceruloplasmin resulting from the recessive disease aceruloplasminemia also have retinal iron accumulation with retinal degeneration.

Disruption in iron homeostasis between the retina and RPE may also cause iron overload. Non-heme iron was found to build up in this debris layer in a time-dependent manner with photoreceptor degeneration, while transferrin levels in the photoreceptor layer were diminished. Photoreceptor loss starts at postnatal day 20 and is significantly increased one month later. In this model, the disruption of normal RPE-photoreceptor interactions leads to an iron homeostasis disorder, which may ultimately contribute to retinal degeneration.

Recent studies suggest that abnormal retinal iron metabolism may promote a variety of retinal disorders. These include ocular siderosis either from intraocular foreign bodies or from intraocular hemorrhage.

Retinal degeneration has also been observed in hereditary disorders resulting in iron overload, including aceruloplasminemia, hereditary hemochromatosis, pantothenate kinase associated neurodegeneration (formerly Hallervorden-Spatz Disease), and Friedreich's Ataxia.

Recently, evidence suggests that iron overload may also play a role in the pathogenesis of age-related macular degeneration (AMD) that leads to vision loss. Possible mechanisms of this vision loss include direct iron toxicity to the photoreceptors, iron toxicity or mechanical damage to the RPE, cellular migration and proliferation in the subretinal space, proliferation of fibrovascular membrane, or separation of photoreceptors from the RPE (Gillies and Lahav, 1983).

Age-related macular degeneration (AMD) is the leading cause of irreversible blindness in developed nations in people age 65 and older (Klein et al., 1995; Leibowitz et al., 1980). Iron may be a source of oxidants in AMD. AMD-affected maculas (n=10) had more iron than healthy agematched maculas (n=9), as demonstrated by an enhanced Perls' Prussian blue stain on sections of the optic disk and macula followed by computer-assisted analysis of digital images to quantify the stain (Hahn et al., 2003).

As age-related macular degeneration may be caused by iron-mediated oxidative damage, it is assumed that antioxidants and iron chelators may be effective in reducing the occurrence and progression of AMD. While the Age-Related Eye Disease Study (AREDS) has shown that supplemental zinc, vitamin C, vitamin E, and β-carotene can provide a protective effect on AMD progression, it is likely that additional antioxidants may further prevent or slow the progression of AMD.

Since iron is one of the most potent generators of oxidative damage through production of hydroxyl radicals in the Fenton reaction, and since the antioxidants used in the AREDS study may not quench all hydroxyl radical produced by iron, it is possible that iron chelators will prove a useful adjunct to AREDS vitamins.

Recent researches suggest that iron chelation may play a role in the treatment of a number of neurological diseases such as Alzheimer's disease and Parkinson's disease, Huntington's disease and Friedreich's Ataxia (Zheng et al., 2005; Richardson, 2004). It is plausible that iron chelation may also be useful in retinal disease associated with iron overload.

Until recently, the only iron chelator in widespread clinical use in the United States was deferoxamine B (DFO), and despite being a relatively effective iron chelator for the treatment of transfusional iron overload, it has many notable limitations. The drug is an inefficient iron chelator, as only 5% or less of the drug administered promotes iron excretion (Bergeron et al., 2002).

In addition, because the iron chelator is poorly absorbed by the gastrointestinal system, and its elimination from the body is rapid, effective DFO treatment requires subcutaneous (SC) or IV administration for 9 to 12 hours for 5 or 6 days each week (Lee et al., 1993; Pippard, 1989). Therefore, for chronic treatment, chelation with DFO is costly, inefficient, cumbersome, and unpleasant.

In addition, DFO administration can have some rare but potentially serious side effects, including pulmonary toxicity, bony changes, growth failure, and promotion of *Yersinia enterocolitica* infections (Tenenbein et al., 1992; Brill et al., 1991; De Virgiliis et al., 1988).

Other iron chelators have been put into clinical use, including deferiprone (L1) and deferasirox (Exjade). Deferiprone has the advantage of being orally active and has been shown to be a more efficient iron chelator than DFO in removing cardiac iron, the cause of most of the mortality in transfusional iron overload (Anderson et al., 2002). A recent report demonstrates the ability of L1 to decrease brain iron in patients with Friedreich's Ataxia (Boddaert et al., 2007). This result suggests that L1 may similarly decrease retinal iron levels.

Deferiprone has rare but serious side-effects, including hepatic fibrosis, agranulocytosis, neutropenia, and arthropathy (Olivieri et al., 1986; Cohen et al., 2003; Ceci et al., 2002). The cause of deferiprone-related side effects is not known, but it may be deferiprone is a bidentate iron chelator.

At low concentrations, bidentate iron chelators can actually facilitate the formation of free-radicals from the formation of incomplete iron chelator complexes (Hershko et al., 2005). Since three molecules of deferiprone are required to completely remove iron from the labile pool, low levels of deferiprone can leave iron incompletely chelated and may cause the unbound portion of iron to be an even more effective catalyst for the generation of free radicals.

Deferasirox is an iron chelator that has just been recently approved for clinical use in patients with iron overload due to blood transfusion. Deferasirox is orally active and has an extended half-life, allowing for once-daily oral dosing (Vanorden and Hagemann, 2006). Current data show deferasirox to be as effective an iron chelator as subcutaneous deferoxamine, which is the current drug of choice for chronic iron overload patients (Piga, et al., 2002).

Another potentially therapeutic iron chelator with interesting properties is salicylaldehyde isonicotinyl hydrazone (SIH). This iron chelator can protect cultured cardiomyocytes from oxidative stress induced death at concentrations 1000 fold lower than DFO (Simunek et al., 2005). However, SIH has poor stability in an aqueous environment due to the rapid hydrolysis of its hydrazone bond.

There are many challenges with using these clinically-available iron chelators to prevent and treat retinal degeneration. Ideally, an iron chelator should be selectively bind iron, but not other biologically important divalent metals such as Zinc (Liu and Hider, 2002).

In addition, an effective iron chelator must reach its target sites at a sufficiently high level. The chelator must be able to be absorbed in sufficient quantity through the gastrointestinal tract, the blood-brain barrier, or in the case of the retina, the blood-retina barrier (BBB). Thus, to successfully penetrate the blood-brain/blood-retinal barrier, an iron chelator must possess appreciable lipid solubility (Kalinowski and Richardson, 2005) and small molecular size, ideally below 500 Daltons (Maxton et al., 1986).

Iron must be carefully regulated to provide necessary iron levels without causing oxidative damage in the photoreceptors, where there is a high oxygen tension and high concentration of easily oxidized polyunsaturated fatty acids, Iron that is not utilized or stored by the cell may be exported by the transport protein ferroportin (also known as MTP-1 or IREG-1) (Donovan et al., 2000; Abboud and Haile, 2000; McKie et al., 2000). Iron is exported by ferroportin in its ferrous state and must be oxidized to be accepted by circulating transferrin.

The oxidation of ferrous iron is accomplished by ferroxidases, ceruloplasmin and hephaestin. Ceruloplasmin is a copper binding protein, which contains over 95% of copper found in plasma. Hephaestin has 50% homology to ceruloplasmin and has ferroxidase activity. Unlike ceruloplasmin, which is present as a secreted plasma protein and glycosylphosphatidylinositol (GPI)-anchored protein (Patel and David, 1997), hephaestin is present only as a membrane-bound protein.

The opposing requirements and toxicities of iron are managed by an iron-responsive mechanism of post-transcriptional regulation of key iron-handling proteins (Hentze and Kuhn, 1996). This regulation allows individual cells to regulate iron uptake, sequestration, and export according to their iron status.

Further, there is no known mechanism of iron excretion from the body. Roughly 1-2 mg of iron is lost daily through sweat, blood loss, sloughing of intestinal epithelial cells, and desquamation. To compensate for this loss, the body absorbs about 1-2 mg of dietary iron per day, but hemoglobin synthesis alone requires 20-25 mg of iron per day.

To support hemoglobin synthesis and other metabolic processes, iron must be recycled and tightly regulated within the system instead of chelation. The circulating peptide hormone hepcidin together with its receptor ferroportin primarily maintain systemic iron homeostasis, whereas iron-regulatory proteins play a primary role in the control of intracellular homeostasis (https://www.ncbi.nlm.nih.gov/pme/articles/PMC4464783/)

The management of iron levels and delivery is also a major challenge. Human cells accumulate iron from two main circulating sources. The first one, which is a classical source, consists of iron bound to transferrin, as described below, and the second one is called Non-Transferrin-Bound Iron (NTBI).

Most cell use transferrin, a serum protein, as a primary staple iron source/transporter. Transferrin comprises a class of biological iron-binding proteins, each lobe bearing a single site capable of reversibly binding iron and accounting for the physiological roles of the proteins in iron transport and iron withholding as a defense against infection.

Tf normally provides iron for cellular needs and for most cells, the delivery of transferrin-borne iron depends on association of the protein with transferrin receptors, TfR1 and TfR2, on plasma membranes. An elaborate receptor-mediated pathway drives endocytosis of Tf-bound iron into mammalian cells for use and storage. Thus, TfR1 and TfR2 play critical roles in iron transfer involving transferrin.

For iron deficient patients, an effective transport of iron from external sources into the cells is required. This requirement is complicated by the fact that environmental iron is invariably present as insoluble iron leading to poor bioavailability and toxicity. Therefore, activators which provide efficient uptake and transport systems to extract iron from their environment and ferritins that store iron in a non-toxic form are required.

Iron-regulatory proteins (IRPs) register intracellular iron status and, in cases of intracellular iron deficiency, bind to iron-responsive elements (IREs) on the mRNA of the regulated protein. Binding of IRPs to the IRE of ferritin sterically obstructs efficient translation, which decreases ferritin levels in iron-deficiency. In contrast, binding of IRP to the IRE of transferrin receptor protects mRNA from degradation, which increases transferrin receptor in iron-deficiency.

Therefore, there is a need for effective intracellular iron regulatory mechanism that can balance and regulate iron within retina cells.

DEFINITIONS

The terminology used herein is for the purpose of describing particular embodiments only and is not intended to be limiting. As used in the specification and the appended claims, the singular forms "a," "and" and "the" include plural references unless the context clearly dictates otherwise.

"About" as used herein may refer to approximately a +/−10% variation from the stated value. It is to be understood that such a variation is always included in any given value provided herein, whether or not specific reference is made to it.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner.

"Pharmaceutically acceptable medium" means a medium that is compatible with the skin, mucous membranes and the integuments.

A "penetration enhancer" is an agent known to accelerate the delivery of the drug through the skin. These agents also have been referred to as accelerants, adjuvants, and absorption promoters, and are collectively referred to herein as "enhancers."

The term "fatty acid" means a fatty acid that has four (4) to twenty-four (24) carbon atoms.

The term "optimizing" to be understood to include balancing, reducing, inhibiting, treating, delaying, improving, and the like.

"Pharmacologically effective amount" means that the concentration of the drug is such that in the composition it results in a therapeutic level of drug delivered over the term that the gel is to be used. Such delivery is dependent on a number of variables including the drug, the form of drug, the time period for which the individual dosage unit is to be used, the flux rate of the drug from the gel, surface area of application site, etc. The amount of drug necessary can be experimentally determined based on the flux rate of the drug through the gel, and through the skin when used with and without enhancers.

"Fixed combination" should be understood as meaning a combination whose active principles are combined at fixed doses in the same vehicle/medium (single formula) that delivers them together to the point of application.

"Treatment" as used herein refers to any treatment of a human condition or disease and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

SUMMARY OF THE DISCLOSURE

While the present invention may be embodied in many different forms, several specific embodiments are discussed herein with the understanding that the present disclosure is considered only as an exemplification of the principles of the invention, and it is not intended to limit the invention to the embodiments illustrated.

The present invention is directed to a pharmaceutical composition for percutaneous administration comprising at least one active pharmaceutical ingredient (e.g., chromium chloride (CrCl3.6H2O)) in a hydroalcoholic gel. In a broad aspect of the invention, the active ingredients employed in the composition may include salt (e.g., magnesium sulfate $(MgSO_4(H_2O)_x)$).

In addition to the active ingredients, the hydroalcoholic gel comprises one or more lower alcohols, such as ethanol or isopropanol; a penetration enhancing agent; a thickening agent; and water. Additionally, the present invention may optionally include emollients, stabilizers, antimicrobials, fragrances, and propellants.

The penetration enhancing agent has a function of improving the solubility and diffusibility of the drug, and those which improve percutaneous absorption by changing the ability of the stratum corneum to retain moisture, softening the skin, improving the skin's permeability, acting as penetration assistants or hair-follicle openers or changing the state of the skin such as the boundary layer.

Further, the penetration enhancing agent herein is a functional derivative of a fatty acid, which includes isosteric modifications of fatty acids or non-acidic derivatives of the carboxylic functional group of a fatty acid or isosteric modifications thereof.

Non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyloleate, isopropyl myristate, butyl stearate, and methyllaurate; di(lower)alkylesters of C6-C8 diacids such as diisopropyl adipate; monoglycerides of C8-C22 fatty acids such as glyceryl monolaurate; tetrahydrofurfuryl alcohol polyethyleneglycol ether; polyethylene glycol, propylene glycol; 2-(2-ethoxyethoxy)ethanol; diethylene glycol monomethylether; alkylarylethers of polyethylene oxide; polyethyleneoxide monomethylethers; polyethylene oxide dimethyl ethers; dimethyl sulfoxide; glycerol; ethyl acetate; acetoacetic ester; N-alkylpyrrolidone; and terpenes.

The thickening agent or thickener used herein may include anionic polymers such as polyacrylic acid (CARBOPOL® by B.F. Goodrich Specialty Polymers and Chemicals Division of Cleveland, Ohio), carboxymethyl cellulose and the like. Additional thickeners, enhancers and adjuvants may generally be found in United States Pharmacopeia/ National Formulary (2000); Remington's The Science and Practice of Pharmacy, Meade Publishing Co.

Because of high lipophilicity, the pharmaceutical composition can be administered topically as chromium chloridereadily enter cells to displace excessive iron from holotransferrin, therefore, is able to efficiently block the production of iron-catalyzed formation.

In one embodiment, iron is known to cause oxidative stress. Elevated iron levels are found in the retinas of patients with age-related macular degeneration, suggesting that iron may play a role in the pathogenesis of neovascular blood vessels. In one embodiment, certain chelators are effective in reducing iron levels in various cell types, including RPE cells; In another embodiment, iron chelation confers cytoprotection against oxidative damage in cardiac myocytes.

In one embodiment, the oxidative stress for which the iron chelator in the methods and compositions described herein, causes age-related macular degeneration, diabetic retinopathy, retinal detachment, subretinal hemorrhage, glaucoma or a combination thereof.

In one embodiment, the chelators most effective at reducing iron levels in RPE cells and their optimal doses are provided herein, and the protective effects of iron chelation against oxidative stress in the human retinal pigment epithelium are described.

In one embodiment, iron overload is also implicated in the retinal degeneration occurring in patients with the rare autosomal recessive disease aceruloplasminemia. These patients have pathologic accumulation of iron in liver, spleen, pancreas, retina, and basal ganglia by the fourth or fifth decade of life.

In one embodiment, provided herein is a method of treating glaucoma in a subject, comprising the step of administering to the subject a composition comprising an effective amount of chromium chloride, magnesium sulfate, or a combination thereof, or in another embodiment, a method of treating diabetic retinopathy in a subject, comprising the step of administering to the subject a composition comprising an effective amount of chromic chloride, magnesium sulfate, or a combination thereof, wherein in one embodiment, the oxidative stress results in apoptosis of retinal cells, and treating comprises reducing incidence, or inhibiting, suppressing or a combination thereof, or wherein treating results in reducing symptoms, ameliorating symptoms, delaying onset, preventing onset, curing said pathology or a combination thereof in other embodiments.

In one embodiment, the methods and compositions described herein are also effective in the treatment of diabetic retinopathy. Sight-threatening diabetic retinopathy is one of the most common complications of diabetes and is the most common cause of vision loss in the under 65 years age group in developed countries, as a result of non-resolving vitreous hemorrhage, traction retinal detachment or diabetic maculopathy.

Sight-threatening diabetic retinopathy refers in one embodiment to diabetic complications affecting the retina that predictably lead to severe loss of vision. These changes include non-resolving vitreous hemorrhage, tractional retinal detachment, or retinal edema.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

DETAILED DESCRIPTIONS OF THE DISCLOSURE

Table 1 shows the ChromicGel comprising the following substances in approximate amounts:3

TABLE 1

Composition of ChromicGel

| SUBSTANCE | AMOUNT (w/w) Per 100 g OF GEL |
|---|---|
| Chromic chloride | 0.002 g |
| Magnesium Sulfate | 10 g |
| Ethanol | 75 g |
| Isopropyl myristate | 0.50 g |
| Purified water (qsf) | 100 g |

One skilled in the art will appreciate that the constituents of this formulation may be varied in amounts yet continue to be within the spirit and scope of the present invention. For example, the composition may contain per 100 g of the composition about 0.002 to about 0.01 g of chromium chloride, about 10.0 to about 25.0 g of magnesium sulfate, about 0.5 to about 5.0 g of isopropyl myristate, and about 75.0 g to about 95.0 g ethanol.

A therapeutically effective amount of the gel is rubbed onto a given area of skin by the user. The combination of the chromium chloride with the hydro-alcoholic gel helps drive the chromium chloride in to the outer layers of the skin where it is absorbed and then slowly released into the blood stream.

Toxicity and therapeutic efficacy of the active ingredients can be determined by standard pharmaceutical procedures, e.g., for determining LD5, (the dose lethal to 50% of the population) and the ED, (the dose therapeutically effective in 50% of the population). The dose ratio between toxic and therapeutic effects is the therapeutic index and it can be expressed as the ratio LD/ED. Compounds which exhibit large therapeutic indices are preferred. While compounds that exhibit toxic effects may be used, care should be taken to design a delivery system that targets such compounds to the site of affected tissue in order to minimize potential damage to uninfected cells and, thereby, reduce side effects.

Although the examples of the present invention involve the treatment of disorders associated with retina neurodegeneration related diseases, the composition and method of the present invention may be used to treat these disorders in humans and animals of any kind, such as dogs, pigs, sheep, horses, cows, cats, zoo animals, and other commercially bred farm animals.

The present invention is further illustrated by the following examples, which should not be construed as limiting in any way. The contents of all cited references throughout this application are hereby expressly incorporated by reference. The practice of the present invention will employ, unless otherwise indicated, conventional techniques of pharmacology and pharmaceutics, which are within the skill of the art.

EXAMPLE 1

Treatment of Diabetic Retinopathy in Human Subjects

The example involves the transdermal application of ChromicGel as a method of treating diabetic retinopathy. As demonstrated below, application of the gel results in a unique pharmacokinetic profile for chromic chloride. Application of the ChromicGel to diabetic retinopathy subjects also results in: (1) increased bone mineral density, (2) increased muscle strength, and (3) better body composition, such increased total body lean mass and decreased total body fat mass. Moreover, the gel is not associated with significant skin irritation.

Methods

In this example, diabetic retinopathy subjects were recruited and studied. The patients were between 50 and 60 years old and had the presence of neovascular blood vessels. A total of 20 patients were enrolled and were randomized to receive 0.002 g/day of ChromicGel 100 g (delivering 0.002 g/day of chromium chloride to the skin of which about 0.002% or 0.002 g is absorbed), and 0.01 g/day of ChromicGel (delivering 0.01 g/day of chromium chloride to the skin of which about 0.01% or 0.01 g is absorbed).

As shown in the following table, there were no significant group-associated differences of the patients' characteristics at baseline.

TABLE 2

Baseline Characteristics of Subjects

| Treatment Group | ChromicGel (0.002 g/day) | ChromicGel (0.01 g/day) |
| --- | --- | --- |
| No of subjects enrolled | 10 | 10 |
| Age (years) | 52.1 | 53.4 |
| Years diagnosed | 1.8 +/- 0.8 | 1.6 +/- 0.5 |

The treatment groups in this example may thus be characterized in two ways, either by "initial" or by the "final" treatment group. Subjects returned to the study center on days 0, 30, 60, and 90 for a clinical examination, skin irritation and adverse event assessments.

EXAMPLE 2

Delivery Dosage Forms and Devices

This example illustrates to a method for dispensing and packaging the gel.

In one embodiment, the invention comprises a hand-held pump capable of delivering about 2.5 g of ChromicGel with each actuation.

In another embodiment, the gel is packaged in foil packets comprising a polyethylene liner. Each packet holds about 10 g, 12.5 g, and 20 g of ChromicGel. The patient simply tears the packet along a perforated edge to remove the gel. However, because isopropyl myristate binds to the polyethylene liner, additional isopropyl myristate is added to the gel in order to obtain a pharmaceutically effective gel when using this delivery embodiment. Specifically, when dispensing the gel via the foil packet, about 41% more isopropyl myristate is used in the gel composition, to compensate for this phenomenon.

The composition can also be dispensed from a rigid multi-dose container (e.g., with a hand pump) having a larger foil packet of the composition inside the container. Such larger packets also comprise a polyethylene liner as above.

Both embodiments permit a patient to deliver accurate but incremental amounts of gel (e.g., either 2.5 g, 5.0 g, 7.5 g, etc.) to the body. These delivery mechanisms thus permit the gel to be administered in unit dose form depending on the particular needs and characteristics of the patient.

EXAMPLE 3

Skin Irritations

Skin irritation assessments were performed at every clinic visit using the following scale:

| | |
| --- | --- |
| 0 | no erythema |
| 1 | minimal erythema |
| 2 | moderate erythema with sharply defined borders |
| 3 | intense erythema with edema |
| 4 | intense erythema with edema and blistering/erosion |

As shown in Table 3, only one patient at 0.005 g/day reported minimal erythema after 60 days, and two patients at 0.01 g/day had minimal erythema after 90 days of treatment.

TABLE 4

Safety Evaluation

| | | Evaluation Time (days) | | |
| --- | --- | --- | --- | --- |
| Initial Treatment Group | N | Day 0 to Day 60 | N | Day 60 to Day 90 |
| 0.002 g/day | 0 | 0 | 0 | 0 |
| 0.005 g/day | 1 | 0.5 +/- 1.4 | 0 | 0 |
| 0.01 g/day | — | — | 2 | 0.4 +/- 1.2 |

Tolerability of the daily application of ChromicGel at the tested dosages was much better than with oral administration. Minimal skin irritation (erythema) at the application site was noted in one patient in the ChromicGel 0.002 g/day group and another two patients in the ChromicGel 0.01 g/day group. No patients who received ChromicGel discontinued the study because of the adverse skin reactions. The open system and the lower concentration of alcohol in the ChromicGel formulation markedly reduced skin irritation resulting in better tolerability and continuation rate on intracellular iron metabolic therapy.

Daily transdermal application of the composition significantly reduces the effect of diabetes on the neurovascular events of the retina and controls diabetes on the neurovascular changes under high serum glucose levels. Long-term treatment further decreases vascular endothelial growth factor (VEGF) expression.

In one embodiment, the present invention provides a composition containing effective amount of chromium chloride ($CrCl_3 \cdot 6H_2O$), magnesium sulfate $MgSO_4$ $(H_2O)_x$ or any combination thereof to optimize and regulate intracellular, which leads to retinal degeneration related-diseases.

EXAMPLE 4

Efficacy Evaluations

As illustrated in Table 4, as a group, overall improvement increased after transdermal ChromicGel treatment without inter-group difference.

TABLE 4

Clinical Evaluation of Efficacy

| Initial Treatment Group | N | Day 0 to Day 60 | N | Day 60 to Day 90 |
|---|---|---|---|---|
| 0.002 mg/day | 10 | 3.2 +/− 1.2 | 1 | 3.6 +/− 1.3 |
| 0.005 mg/day | 10 | 3.1 +/− 1.4 | 5 | 3.4 +/− 1.6 |
| 0.01 mg/day | — | — | 14 | 3.8 +/− 1.4 |

0 = no response
1 = slight improvement
2 = good improvement
3 = very good improvement
4 = dramatic improvement The randomized and parallel study compared two doses of ChromicGel. For two months of the study (days 1 to 60), twenty subjects were randomized to receive 0.002 g/day of ChromicGel and 0.005 g/day of ChromicGel. Subjects who were applying ChromicGel once a day had a single, pre-application vascular endothelial growth factor (VEGF) levels measured on day 60 and, if the levels remained stabilized within the normal range, then they remained on their original dose. Subjects with VEGF levels, which were in continuous progressive state, were then reassigned to administer twice a day of 0.01 g ChromicGel for days 60 to 90.

Accordingly, at 60 days, dose adjustments were made in the ChromicGel groups based on the pre-application VEGF levels on day 60. Nine subjects in the 0.002 g/day ChromicGel group had the dose increased to 0.01 g twice a day. Five subjects in the 0.005 g/day ChromicGel group had the dose increased to 0.01 g twice a day.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A composition comprising:
    (a) about 0.002% to about 0.01% chromic chloride;
    (b) about 10% to about 25% magnesium sulfate;
    (c) about 75% to about 95% ethanol;
    (d) about 0.5% to about 5% isopropyl myristate; and
    (e) about 0.1% to about 6% of a thickening agent,
    wherein the percentages of components are weight to weight of the composition.

2. The composition of claim 1, wherein the chromic chloride is present in a concentration selected from the group consisting of about 0.002%, 0.005%, and 0.01% weight to weight of the composition.

3. The composition of claim 1, wherein the thickening agent is selected from the group consisting of polyacrylic acid and carboxymethylcellulose.

4. The composition of claim 1, wherein the composition is the form of a gel.

5. A unit dose packet comprising inner and outer surface, and a pharmaceutical composition inside the packet, the composition comprising:
    (a) about 0.002% to about 0.01%, chromium chloride;
    (b) about 10% to about 25% magnesium sulfate;
    (c) about 75% to about 95% ethanol;
    (d) about 0.5% to about 5% isopropyl myristate; and
    (e) about 0.1% to about 6% of a thickening agent,
    wherein the percentages of components are weight to weight of the composition.

6. The packet of claim 5, wherein the composition weighs about 10.0 grams to 20.0 grams.

7. The packet of claim 5, wherein the composition weighs about 12.5 grams to 15.0 grams.

8. The packet of claim 5, wherein the chromium chloride is present in a concentration selected from the group consisting of about 0.002%, 0.005%, and 0.01% weight to weight of the composition.

9. The packet of claim 5, wherein the magnesium sulfate is present in a concentration selected from the group consisting of 5%, 10%, 15%, 20%, and 25% weight to weight of the composition.

10. The packet of claim 5, wherein the thickening agent is selected from the group consisting of polyacrylic acid and carboxymethylcellulose.

11. The composition of claim 5, wherein the composition is the form of a gel.

12. A method for topically administering chromium chloride to a human subject in need thereof, the method comprising:
    providing a pharmaceutical composition comprising;
        (i) about 0.002% to about 0.01% chromium chloride;
        (ii) about 10% to about 25% magnesium sulfate;
        (iii) about 75% to about 95% ethanol;
        (iv) about 0.5% to about 5% isopropyl myristate; and
        (v) about 0.1% to about 6% of a thickening agent,
    wherein the percentages of components are weight to weight of the composition;
    and
    applying a daily dose of the composition to the skin of the subject in an amount sufficient for the chromium chloride to reach the bloodstream of the subject within at least 48 hours of daily dosing of the composition.

13. The method of claim 12, wherein the chromium chloride is present in a concentration of about 0.005% weight to weight of the composition.

14. The method of claim 13, wherein the chromium chloride is present in a concentration of about 0.01% weight to weight of the composition.

15. The method of claim 13, wherein the isopropyl myristate is present in a concentration of about 0.2% weight to weight of the composition.

16. The method of claim 13, wherein the ethanol is present in a concentration of about 65.5% weight to weight of the composition.

17. The method of claim 13, wherein the thickening agent is present in a concentration of about 0.5% weight to weight of the composition.

18. The method of claim 13, wherein the composition is the form of a gel.

* * * * *